(12) United States Patent
Kojima et al.

(10) Patent No.: US 6,268,166 B1
(45) Date of Patent: *Jul. 31, 2001

(54) METHOD OF QUANTITATIVE ASSAY FOR 1,5-ANHYDROGLUCITOL

(75) Inventors: Ryo Kojima; Yoshiro Sato, both of Koriyama; Takeshi Nagasawa, Urawa, all of (JP)

(73) Assignee: Nitto Boseki Co., LTD, Fukushima (JP)

( * ) Notice: Subject to any disclaimer, the term of this patent is extended or adjusted under 35 U.S.C. 154(b) by 0 days.

This patent is subject to a terminal disclaimer.

(21) Appl. No.: 08/230,440

(22) Filed: Apr. 19, 1994

Related U.S. Application Data

(63) Continuation of application No. 07/991,141, filed on Dec. 16, 1992, now abandoned.

(30) Foreign Application Priority Data

Dec. 18, 1991 (JP) .................................................... 3-334892
Mar. 2, 1992 (JP) .................................................... 4-044715

(51) Int. Cl.[7] ................................ C12Q 1/26; C12Q 1/00; C12Q 1/32
(52) U.S. Cl. .................................... 435/25; 435/4; 435/26; 435/14; 435/28; 435/283.1
(58) Field of Search .......................... 435/25, 4, 26, 435/14, 28, 11, 283.1

(56) References Cited

U.S. PATENT DOCUMENTS

| | | | |
|---|---|---|---|
| 4,636,464 | * 1/1987 | Nakanishi et al. | 435/14 |
| 4,810,640 | 3/1989 | Nakamura et al. | 435/25 |
| 4,873,195 | * 10/1989 | Kubo et al. | 435/254 |
| 4,994,377 | * 2/1991 | Nakamura et al. | 435/25 |

FOREIGN PATENT DOCUMENTS

| | | | |
|---|---|---|---|
| 0 261 591 A2 | * 3/1988 | (EP) | C12Q/1/00 |
| 2-42980 | 8/1988 | (JP) | C12N/9/04 |
| 63-256416 | * 10/1988 | (JP) . | |
| 2-104298 | 10/1988 | (JP) | C12Q/1/48 |

OTHER PUBLICATIONS

*Chemical Patents Index, Documentation Abstracts of Journal D*, Derwent Publications 1990; No. 90–161279/21, JO 2104–298–A, Oct. 13, 1988.*

Fukumura, Yukihito et al., Interference of Maltose for the Determination of 1,5–Anhydroglucitol with Lana AGε Kit, Rhinsho Kagku (Nippon Rinsho Kagaki), 21 (1992), pp. 43–48, month not available.*

*Journal of Japanese Internal Medicine 80*:1198–1204, 1991. Month not available.

Yoshioka et al., *J. Japan. Diab. Soc.* 25(10):1115–1118, 1982. Abstract only. Month not available.

Kawai, *Japanese Clinic* 47:439–442, 1989. Month not available.

Izumi et al., *Agric. Biol. Chem.* 54(3):799–801, 1990. Month not available.

Izumi et al; "Purification & Properties of Pyranose Oxidase from Basidiomycetous Fungus No. 52"; Agricultural and Biological Chemistry; 54(6), 1393–1399, 1990, month not available.*

* cited by examiner

Primary Examiner—Louise N. Leary
(74) Attorney, Agent, or Firm—Darby & Darby

(57) ABSTRACT

There is provided an enzymatic method of rapid quantitative assay for 1,5-anhydroglucitol which is also applicable to an automated analysis device. The enzymatic method of quantitative assay for 1,5-anhydroglucitol is characterized by using a pyranose oxidase derived from *Basidiomycetous fungi* No. 52 as a pyranose oxidase. According to the assaying method of the present invention, assay for 1,5-anhydroglucitol in a specimen can be performed using an automated analysis device, results in rapid assay and improved accuracy.

6 Claims, 3 Drawing Sheets

OPTIMUM PH OF PROD DERIVED FROM BASIDIOMYCETOUS FUNGI NO.52

TIME COURSE FOR ASSAY REACTION
(MODEL 7150, AUTOMATED ANALYSIS DEVICE)

CALIBRATION CURVE OF 1,5-AG AND GLUCOSE REMOVAL ABLITY OF REACTION SYSTEM

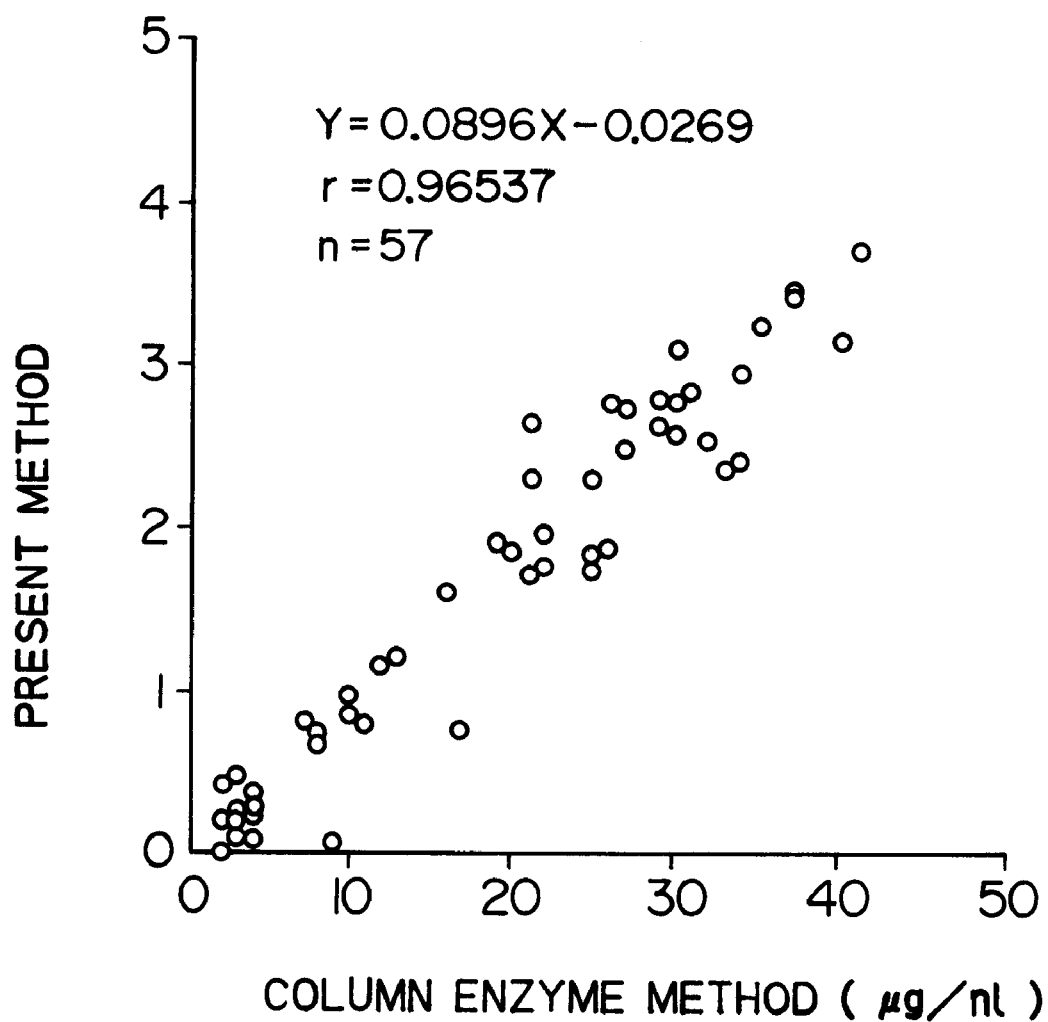

METHOD OF QUANTITATIVE ASSAY FOR 1,5-ANHYDROGLUCITOL

This is a continuation of application Ser. No. 07/991,141, filed Dec. 16, 1992, now abandon.

FIELD OF THE INVENTION

The present invention relates to a method of enzymatic assay for 1,5-anhydroglucitol (hereafter referred to as "1,5-AG"), which is expected as a marker for diagnosis of diabetes, in a simple and rapid way. This method is also applicable to an automated analysis device.

BACKGROUND OF THE INVENTION

Prior Art Statement 1,5-AG is a compound which is present in the cerebrospinal fluid and plasma of humans. It is reported that its quantity is markedly reduced in plasma with certain diseases, particularly with diabetes (Yasuo Akanuma, Kazuyuki Tobe: Journal of Japanese Internal Medicine Association, 80, 1198–1204, 1991), 1,5-AG is expected to be as a marker for diagnosis of diabetes.

As assay for 1,5-AG, there are hitherto known a method based on gas chromatography (Yoshioka, Diabetes, 25, 1115–1118, 1982; hereafter referred to as "GC method") and methods using enzymes (hereafter referred to as "enzymatic methods") such as pyranose oxidase (hereafter abbreviated as PROD) or L-sorbose oxidase (Japanese Patent KOKAI (Laid-Open) No. 63-185397).

Serum or plasma collected from the patient with diabetes is mainly a specimen to be assayed for 1,5-AG. In blood from the patient with diabetes, its glucose concentration is higher than that of normal person. In blood from normal person, the glucose concentration is in the range of approximately 60 to 100 mg/dl, whereas in blood from the patient with diabetes, the glucose concentration is widely distributed in the range of 100 to 1000 mg/dl. On the other hand, the concentration of 1,5-AG in blood is in the range of 1.64 to 2.68 mg/dl for normal person but in the patient with diabetes its concentration is as extremely low as 0.18 to 0.21 mg/dl (Japanese Clinic, 47, 1089, extra issue, Immunological Inspection in Blood and Urinary Chemical Test over Wide Range; first volume, 439–442, Kawai). Therefore, the concentration of 1,5-AG in blood from the patient with diabetes becomes about 1/470 or less. In addition, glucose is structurally similar to 1,5-AG so that it is impossible to perform selective assay in the presence of 1,5-AG and glucose on the current technical level. It is thus essentially required to selectively remove glucose or pretreat specimen by adequately modifying the specimen.

In the GC method, the pretreatment requires removal of glucose and labeling of 1,5-AG which makes procedures complicate and involves analysis over long periods of time. For these reasons, it is difficult to assay a large number of specimens by the GC method. There are thus problems for applying the method to clinical assay.

In the enzymatic method, the pretreatment is performed by removing glucose using an ion exchange column or by modifying glucose through phosphorylation. The enzymatic method is accompanied by considerably complicated separation procedures when glucose is removed using an ion exchange column. Turning to glucose modification by phosphorylation, the optimum reaction conditions for phosphorylation including difference in the optimum pH differ from the optimum conditions for reactions of quantitative assay for 1,5-AG. Therefore, phosphorylation and assay for 1,5-AG must be carried out under different reaction conditions, respectively. In addition, adenosine-5'-triphosphate (hereafter referred to as "ATP") used for phosphorylation has an inhibitory action against PROD. In view of concentration, there is a limit in adding ATP to the assay system for accelerating phosphorylation and hence, it was difficult to terminate phosphorylation rapidly. In any event, it is impossible to perform quantitative assay rapidly by the prior art methods. In particular, any of the prior art methods has not come to be applied to an automated analysis device widely used for various clinical tests.

SUMMARY OF THE INVENTION

An object of the present invention is to eliminate the foregoing shortcomings of the prior art methods of assay for 1,5-AG in a specimen described above and provide a method of quantitative assay for 1,5-AG in a simple and rapid manner without requiring separation procedures such as filtration, centrifugation, adsorption, etc.

Another object of the present invention is to provide a method of assay for 1,5-AG using an automated analysis device.

In order to solve the foregoing problems the present inventor has made extensive investigations and as a result, succeeded in solving the problems. That is, by selecting a more appropriate enzyme than PROD as an enzyme acting on 1,5-AG, the inhibitory reaction of PROD by ATP can be avoided and reaction conditions for phosphorylation can be harmonized with reaction conditions for quantitatively assaying 1,5-AG. The present invention has thus been accomplished.

A first aspect of the present invention is to provide a method of quantiative assay for 1,5-AG using as PROD the one derived from *Basidiomycetous fungi* No. 52.

A second aspect of the present invention is to provide a method of quantitative assay for 1,5-AG which comprises selectively removing sugars other than 1,5-AG in a specimen so as to leave 1,5-AG and quantitatively assaying 1,5-AG using PROD derived from *Basidiomycetous fungi* No. 52.

A third aspect of the present invention is to provide a method of quantitative assay for 1,5-AG which enables to perform the aforesaid selective removal of sugars other than 1,5-AG and quantitative assay for 1,5-AG subsequent thereto in a pH range of 6 to 9.

A fourth aspect of the present invention is to provide a method of quantitative assay for 1,5-AG in which comprises effecting the selective removal of sugars other than 1,5-AG using a large excess of ATP and then quantitatively assaying 1,5-AG.

BRIEF DESCRIPTION OF THE DRAWINGS

FIG. 5 shows correlation of the method of the present invention with the column enzyme method.

DETAILED DESCRIPTION OF PREFERRED EMBODIMENTS

Figure 1:
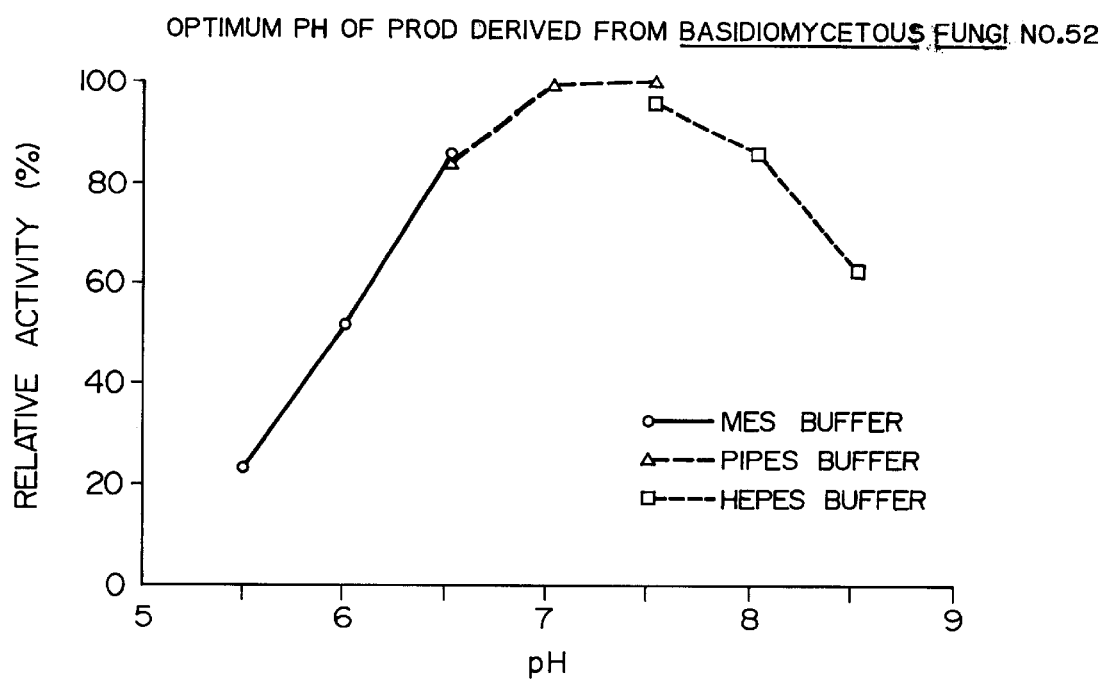
FIG. 1 is a curve showing the optimum pH of PROD derived from *Basidiomycetous fungi* No. 52 to 1,5-AG in good buffer solution.

Hereinafter the present invention will be described in detail.

The specimen in the present invention is used to mean any specimen; there is no particular restriction so long as one wishes to quantitatively determine the concentration of 1,5-AG in the specimen. Examples of such specimen include blood, plasma, etc.

The PROD used in the present invention is a PROD derived from *Basidiomycetous fungi* No. 52 (hereafter referred to specifically as "Bf-PROD") *Basidiomycetous fungi* No. 52 is a strain belonging to Basidiomycetes which was deposited on Jun. 27, 1988 in the Fermentation Research Institute of the Agency of industrial Science & Technology of Japan under Accession No. FERM P-10106. *Basidiomycetous fungi* No. 52 is further reported in Japanese Patent KOKAI (Laid-Open) No. 2-42980, Yoshikazu Izumi et al., Agric. Biol. Chem., 54 (6) 799–801 (1990) and Yoshikazu Izumi et al., Agric. Biol. Chem., 54 (6) 1393–1399 (1990), and is therefore well known to a person skilled in the art. This strain grows in the pH range of 3 to 8 at the optimum growth temperature of 30° C. under aerobic conditions; either asexual spore such as conidium or sexual spore such as basidiospore is not observed. Bf-PROD obtained from this strain is a glycoprotein having a molecular weight of about 300,000 and an isoelectric point of 6.2 when measured by gel filtration and focusing electrophoresis, respectively, and stained to reddish purple by PAS staining.

The enzymological properties of Bf-PROD on 1,5-AG verified by the present inventor are as follows:

optimum pH: 7.0–8.0 pH range at which the enzyme has its activity: 6–9 temperature range at which the enzyme has its activity: 25–40° C.

In addition, the enzyme hardly undergoes the inhibitory action by ATP upon oxidation of 1,5-AG.

In quantitative assay for 1,5-AG in specimen, sugars other than 1,5-AG which are present in the specimen are selectively removed. The sugars other than 1,5-AG in a specimen refer mainly to glucose and also to obtain sugars phosphorylated by hexokinase.

For selectively removing the sugars in a specimen, it is preferred to choose methods by which the sugars such as glucose can be eliminated in a reaction solution without relying upon any solid phase. Such methods are known in the art and include a method which comprises degrading the sugars with 6N hydrochloric acid, reduction with sodium borohydride, a method Eor converting glucose into gluconic acid with glucose oxidase, a method for phosphorylation of the sugars with hexokinase. Among them, the most preferred is the method for phosphorylation of the sugars with hexokinase since substances participating in selective removal of the sugars and the reaction product do not affect the reaction for quantitative determination of 1,5-AG and the reaction can be completed in a short period of time.

The automated analysis device or equipment collectively termed in the present invention is specifically exemplified by Model 7050, Model 705 and Model 736 manufactured by Hitachi Ltd., etc. The automated analysis device is not limited to these specific equipments but any devices equivalent thereto are usable in the present invention.

As the hexokinase which is used for phosphorylation of sugars including conversion of glucose into glucose-6-phosphate, it is preferred to use a hexokinase classified as EC 2.7.1.1 according to the classification defined by International Biochemical Association. In this conversion, ATP and magnesium ions are used together with the enzyme. As sources of magnesium ions there may be used organic acid salts such as magnesium fatty acid salts, magnesium acetate, etc., and inorganic acid salts such as halides, sulfates, nitrates, phosphates, etc. Among them, acetates and hydrochlorides are preferred.

The hexokinase, ATP and magnesium ions are used in the reaction described above in the optimum amounts, namely, 5 to 100 U/ml of hexokinase, 5 to 500 mM of ATP and 5 to 50 mM of magnesium ions. The optimum pH for the reaction is 7.5 but may also be allowable in the range of 6 to 9.

In the present invention, PROD derived from *Basidiomycetous fungi* No. 52 is used as PROD for quantitative assay for 1,5-AG. This PROD is hardly susceptible to inhibition by ATP. Therefore, ATP can be used in a large excess, e.g., in an amount of 100 mM to 500 mM, for the reaction of removing sugars. Then, the next enzymatic reaction with PROD can be proceeded as it is, without removing ATP.

Furthermore, the PROD derived from *Basidiomycetous fungi* No. 52 which is used in the present invention is reactive with 1,5-AG in the pH range of 6 to 9. It is thus possible to quantitatively assaying 1,5-AG in the same pH range as required for the reaction of removing sugars.

According to the present invention, therefore, the reaction of removing sugars and the enzymatic reaction of 1,5-AG can be performed under the same pH conditions, e.g., in the pH range of 7.0 to 8.0 and these reactions can also be carried out continuously in an extremely short period of time. The method of quantitative assay for 1,5-AG of the present invention is extremely efficiently applicable to an automated analysis device.

After sugars are selectively removed, 1,5-AG remained in a specimen is assayed by the action of PROD thereon. By reacting PROD with 1,5-AG, hydrogen peroxide generates. The hydrogen peroxide is acted on a known peroxides substrate such as 2,2'-azinobis-(3-ethylbenzothiazoline-6-sulfonic acid), o-phenylenediamine, 5-aminosalicylic acid, 3,3',5,5'-tetramethylbenzidine, combination of 4-aminoantipyrine and N-ethyl-N-(2-hydroxysulfopropyl)-m-toluidine, using an enzyme classified as EC 1.11.1.7 according to the classification by International Biochemical Association. Absorbance of the dye thus produced from the substrate is measured.

The peroxidase used for determining hydrogen peroxide is preferably horse radish peroxidase. As the substrate used to produce the dye for measurement of absorbance, the combination of 4-aminoantipyrine and N-ethyl-N-(2-hydroxysulfopropyl)-m-toluidine is preferred. When using the combination of 4-aminoantipyrine and N-ethyl-N-(2-hydroxysulfopropyl)-m-toluidine, its wavelength in the absorbance measurement region is in the range of 500 nm to 800 nm. Within this range, two or more wavelengths may be used for measurement.

Preferred amount of PROD, horse radish peroxidase, 4-aminoantipyrine and N-ethyl-N-(2-hydroxysulfopropyl)-m-toluidine used in the reaction described above are in the following ranges, respectively: 5 to 500 U/ml of PROD, 2 to 20 U/ml of horse radish peroxidase, 0.1 to 10 mM of 4-aminoantipyrine and 0.1 to 10 mM of N-ethyl-N-(2-hydroxysulfopropyl)-m-toluidine. An effective pH range of the reaction is about 7.5 as in the case of hexokinase, and it is possible to carry out the reaction in the range of pH 6–9.

Throughout the reactions for assaying 1,5-AG in a specimen, the reaction temperature is kept between 5 and 40° C., preferably between 25 and 40° C. The reaction time is 2 to 60 minutes, preferably 2 to 30 minutes. During the course of preparing the reaction solution, the reaction as a whole proceeds at pH of 7.0 to 8.0, preferably 7.5 to 8.0. Therefore, in order to stabilize the reaction solutions of reagents in the pH range of 7.0 to 8.0, preferably 7.5 to 8.0, in the maximum range of 6 to 9, phosphate buffer, Tris hydrochloride buffer, HEPES buffer, etc. are used as buffer solutions. When HEPES buffer is used, it is preferred to keep its concentration in the range of 50 to 500 mM. For controlling ionic intensity, halogenated alkali metal salts, preferably sodium chloride, etc. may be used. BY performing the whole reactions at a pH of 6 to 9, preferably 7.0 to 8.0 using as PROD Bf-PROD described in Japanese Patent KOKAI (Laid-Open) No. 2-42980, phosphorylation of sugars such as glucose contained in a specimen and the color forming reaction for measuring hydrogen peroxide generated by the action of PROD can be completed both in 5 minutes.

Where 1.5-AG is asaayed according to the method of the present invention, the respective components described above may be incorporated in one solution; alternatively, the respective components may also be used in appropriate combination. These components may be either in a solution form or freeze-dried. Where it is intended to store them over a long period of time, the components may preferably be freeze-dried. It is also possible to add a surface active agent within such a concentration range that does not inhibit the assay reaction. Where the measurement system is freeze-dried, a stabilized may be added in an appropriate amount.

Hereafter the present invention is described in more detail with reference to the examples.

EXAMPLE 1

Optimum pH of PROD to 1,5-AG

The optimum pH of Bf-PROD to 1,5-AG was determined. The results are shown in FIG. 1. The reaction conditions for the determination are as follows.

After 280 μl of the first reagent having the following composition and 70 μl of the second reagent having the following composition were added to 10 μl of 1000 U/l of PROD solution, the reaction was carried out. Change in absorbance was treated between 30 to 40 points for measurement at a main wavelength of 546 nm and a side wavelength of 700 nm, using automated analysis device, Hitachi Model 7150 by the function of the analysis device. A relative activity is shown when the maximum change in absorbance (pH=7.5) obtained was made 100%.

As shown in FIG. 1, PROD shows the highest activity of 1,5-AG in Good buffer solution in the pH ange of 7.0 to 8.0.

| First Reagent | |
|---|---|
| First reagent in the pH range of 5.5 to 6.5 | |
| MES | 200 mM |
| Sodium chloride | 150 mM |
| Magnesium acetate | 10 mM |
| N-Ethyl-N-(2-hydroxysulfopropyl)-m-toluidine | 1 mM |
| Peroxidase | 5 KU/l |
| Hexokinase | 20 KU/l |
| First reagent in the pH range of 6.5 to 7.5 | |
| PIPES | 200 mM |
| Sodium chloride | 150 mM |
| Magnesium acetate | 10 mM |

-continued

| First Reagent | |
|---|---|
| N-Ethyl-N-(2-hydroxysulfopropyl)-m-toluidine | 1 mM |
| Peroxidase | 5 KU/l |
| Hexokinase | 20 KU/l |
| First reagent in the pH range of 7.5 to 8.5 | |
| HEPES | 200 mM |
| Sodium chloride | 150 mM |
| Magnesium acetate | 10 mM |
| N-ethyl-N-(2-hydroxysulfopropyl)-m-toluidine | 1 mM |
| Peroxidase | 5 KU/l |
| Hexokinase | 20 KU/l |

| Second Reagent | |
|---|---|
| 4-Aminoantipyrine | 4 ml |
| Sodium chloride | 150 ml |
| 1,5-AG | 100 ml |
| Buffer agent | none |

EXAMPLE 2

Change in pH of Inhibition of PROD by ATP

The degree of the reaction of Bf-PROD with 1,5-AG affected by ATP was examined in Good buffer in the pH range of 5.5 to 8.5.

After 280 μl of the first reagent having the following composition and 70 μl of the second reagent having the following composition were added to 10 μl of 1000 U/l of PROD solution, the reaction was carried out. Change in absorbance was traced between 30 to 40 points for measurement at a main wavelength of 546 nm and a side wavelength of 700 nm, using automated analysis device, Hitachi Model 7150 by the function of the analysis device.

The inhibition degree by ATP is shown in terms of PROD activity as a relative activity where ATP was present in the same pH, when PROD activity was made 100% where ATP was absent under the conditions that 100 mM ATP was newly added to buffer of each pH. The results obtained are shown in FIG. 2.

Figure 2:
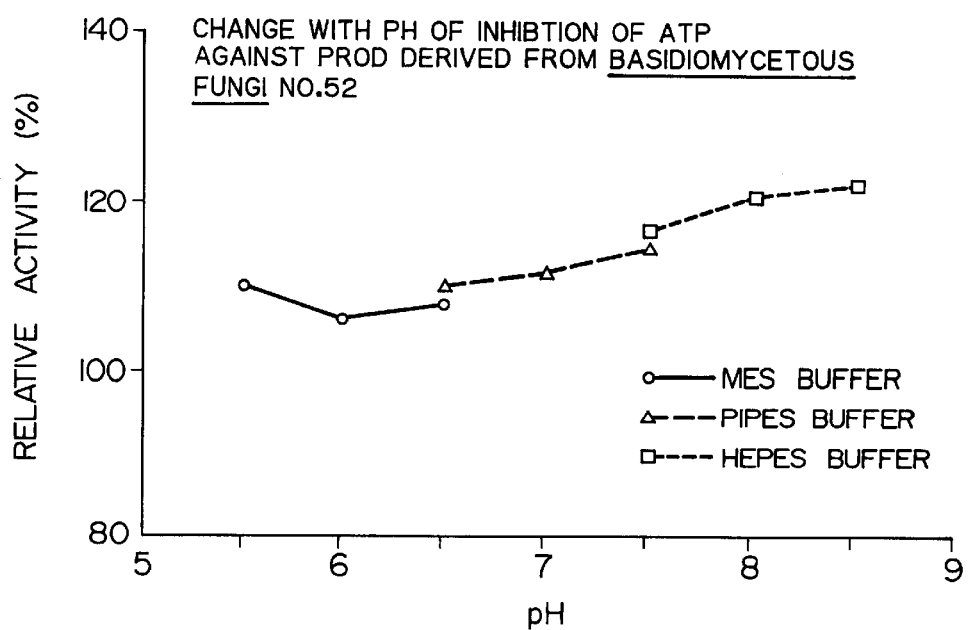
FIG. 2 shows a change with pH of inhibition of ATP against PROD derived from *Basidiomycetous fungi* No. 52.

As shown in FIG. 2, PROD was not affected by ATP in Good buffer but its activity was rather increased. This tendency was more remarkable as pH increased.

From the results shown in FIGS. 1 and 2, it is evident that Bf-PROD is not affected by ATP at all but its activity is rather potentiated and Bf-PROD shows good reactivity with 1,5-AG. Therefore, glucose can be efficiently phosphorylated in such a pH range, preferably at pH of 7.5 and the reaction for detecting 1,5-AG can be subsequently performed satisfactorily.

| First Reagent | |
|---|---|
| First reagent in the pH range of 5.5 to 6.5 | |
| MES | 200 mM |
| Sodium chloride | 150 mM |
| Magnesium acetate | 10 mM |
| N-Ethyl-N-(2-hydroxysulfopropyl)-m-toluidine | 1 mM |
| Peroxidase | 5 KU/l |

-continued

| First Reagent | | |
|---|---|---|
| Hexokinase | 20 | KU/l |
| ATP | 0 | mM |
| or | 100 | mM |
| First reagent in the pH range of 6.5 to 7.5 | | |
| PIPES | 200 | mM |
| Sodium chloride | 150 | mM |
| Magnesium acetate | 10 | mM |
| N-Ethyl-N-(2-hydroxysulfopropyl)-m-toluidine | 1 | mM |
| Peroxidase | 5 | KU/l |
| Hexokinase | 20 | KU/l |
| ATP | 0 | mM |
| or | 100 | mM |
| First reagent in the pH range of 7.5 to 8.5 | | |
| HEPES | 200 | mM |
| Sodium chloride | 150 | mM |
| Magnesium acetate | 10 | mM |
| N-Ethyl-N-(2-hydroxysulfopropyl)-m-toluidine | 1 | mM |
| Peroxidase | 5 | KU/l |
| Hexokinase | 20 | KU/l |
| ATP | 0 | mM |
| or | 100 | mM |

| Second Reagent | | |
|---|---|---|
| 4-Aminoantipyrine | 4 | mM |
| Sodium chloride | 150 | mM |
| 1,5-AG | 100 | mM |
| Buffer agent | none | |

EXAMPLE 3

Time Course of Measurement Reaction in the Present Invention

Figure 3:
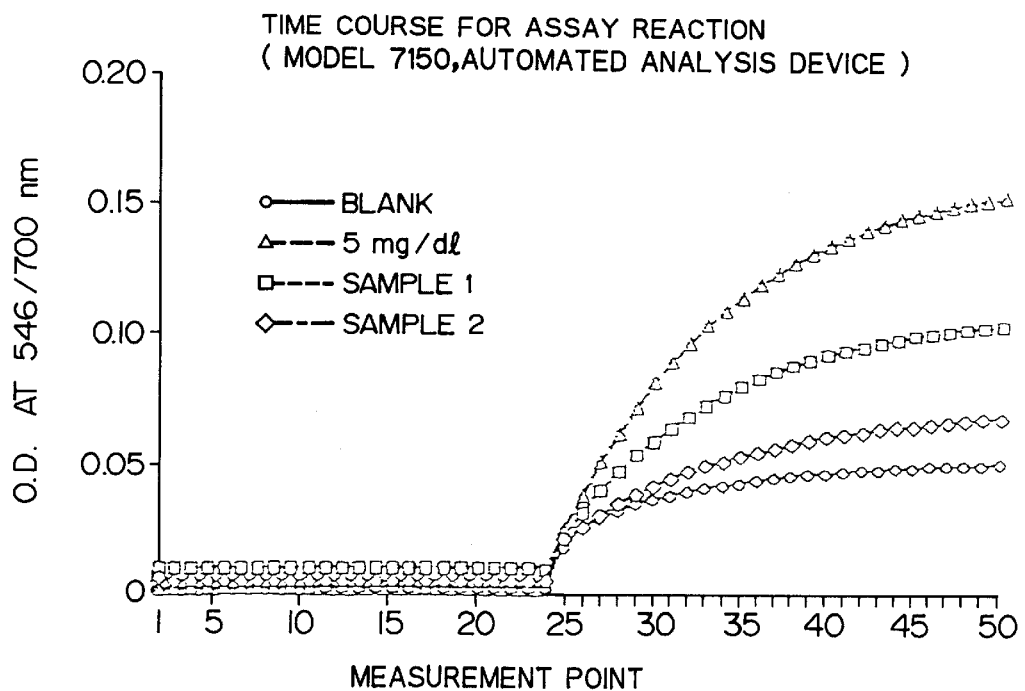
FIG. 3 shows time course for assay reaction in the present invention.

Physiological saline as blank control, 5 mg/dl of 1,5-AG aqueous solution and two kinds of human serum (Sample Nos. 1 and 2) were used as specimens. Each specimen was reacted with the first and second reagents having the following compositions, whereby reacticon time course was measured. The results are shown in FIG. 3.

The reaction conditions are as follows: 7 μl of specimen, 280 μl of the first reagent and 70 μl of the second reagent were used and the assay was made at two points at main wavelength of 546 nm and side wavelength of 700 nm, using automated analysis device, Hitachi Model 7150. The measurement reaction was completed in almost 5 minutes.

| First Reagent | | |
|---|---|---|
| HEPES | 200 | mM |
| Sodium chloride | 150 | mM |
| Magnesium acetate | 10 | mM |
| N-Ethyl-N-(2-hydroxysulfopropyl)-m-toluidine | 1 | mM |
| Peroxidase | 5 | KU/l |
| Hexokinase | 20 | KU/l |
| ATP | 100 | mM |
| pH 7.5 | | |

| Second Reagent | | |
|---|---|---|
| HEPES | 200 | mM |
| Sodium chloride | 150 | mM |
| 4-Aminoantipyrine | 4 | mM |
| PROD | 62.5 | KU/l |
| pH 7.5 | | |

EXAMPLE 4

Calibration Curve of 1,5-AG and Removal of Glucose in Specimen

Figure 4:
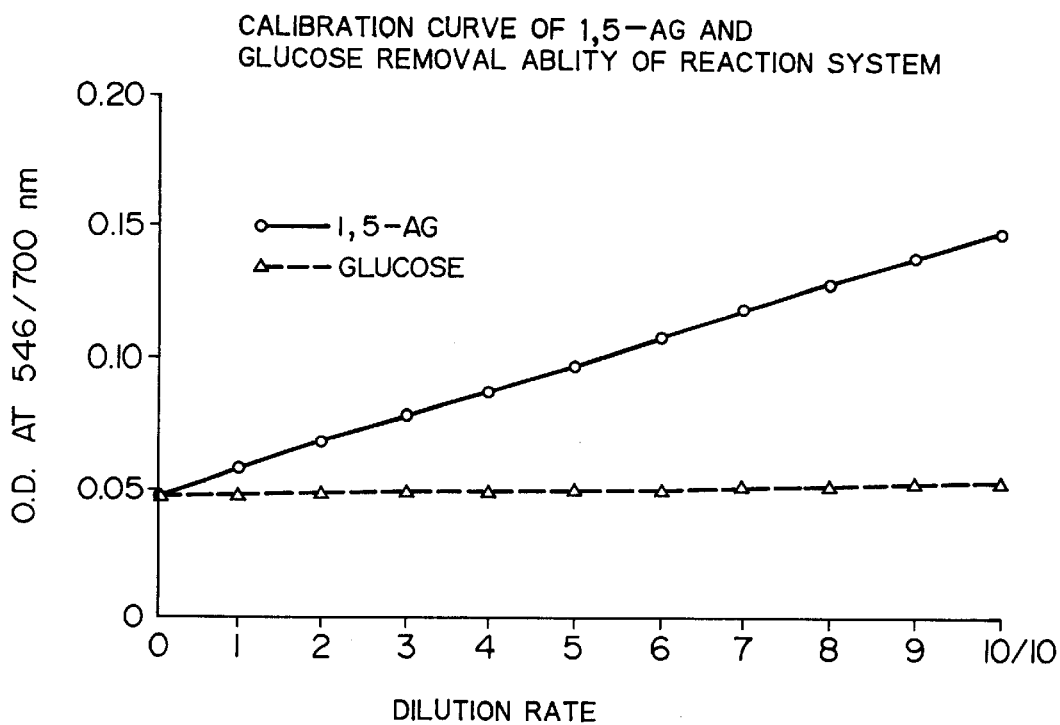
FIG. 4 shows a calibration curve of 1,5-AG and also shows glucose removal ability of the reaction system.

Under the measurement conditions of Example 3,0 to 5 mg/dl of 1,5-AG aqueous solution prepared in concentration by 0.5 mg/dl difference was reacted and each absorbance was measured. The results are shown in FIG. 4. Furthermore, 0 to 1500 mg/dl of glucose aqueous solution prepared in concentration by 150 mg/dl difference was reacted in a similar manner and each absorbance was measured. The results are also shown in FIG. 4.

As is noted from FIG. 4, there was a good linearity up to 5 mg/dl which crosses the origin when 1,5-AG was reacted. Where glucose was reacted, almost the same absorbance as in reagent blank was obtained up to 1500 mg/dl, indicating that glucose was almost completely erased up to 1500 mg/dl. It can thus be judged that glucose was satisfactorily erased and good quantitative assay for 1,5-AG can be made under the measurement conditions in this Example.

EXAMPLE 5

Test for Recovery of 1,5-AG Added

Using sera collected from patients having known concentrations of 1,5-AG, 1,5-AG was added to the sera. Each of the thus obtained specimens was reacted under the conditions of Example 3 described above. 1,5-AG was quantitatively assayed using the calibration curve obtained in the foregoing Example.

The data actually obtained (amount found) was divided by the sum (theoretical amount) of the 1,5-AG content in the patient's serum and the amount of 1,5-AG added. The thus obtained value is made recovery rate. The results are shown in Table 1.

TABLE 1

Recovery Rate of 1,5-AG Added

| Serum from Patient (mg/dl) | Amount Added (mg/dl) | Theoreical Amount (mg/dl) | Amount Found (mg/dl) | Recovery Rate (%) |
|---|---|---|---|---|
| 0.19 | 1.15 | 1.34 | 1.35 | 100.7 |
| | 3.07 | 3.26 | 3.22 | 98.8 |
| 0.43 | 1.15 | 1.58 | 1.53 | 96.8 |
| | 3.07 | 3.50 | 3.47 | 99.1 |
| 0.94 | 1.15 | 2.09 | 2.04 | 97.6 |
| | 3.07 | 4.01 | 3.99 | 99.5 |
| 1.48 | 1.15 | 2.63 | 2.58 | 98.1 |
| | 3.07 | 4.55 | 4.54 | 99.8 |
| | | | Average | 98.8 |

Average recovery rate was almost 100%, indicating that the method of the present invention is highly accurate.

EXAMPLE 6

Correlation with Conventional Method

Correlation in measurement data of the enzymatic method of the present invention with conventional enzymatic method using ion exchange column which had been considered to be highly reliable method for quantitative determination of 1,5-AG (hereafter referred to as "column enzyme method") was examined. In the column enzyme method, 57 human serum specimens were assayed following the manual, using LANA AG (registered trademark) manufactured by Nippon Kayaku Co., Ltd. In the enzymatic method of the present invention, the same human sera as used in the column enzyme method were used as specimens and provided for quantitative assay in the same manner as in Example 3, using the calibration curve prepared in Example 4. The results are shown in FIG. 5. The correlation coefficient was 0.97, indicating that there was high correlation between the two methods.

As shown in the foregoing Examples, the method of quantitative assay for 1,5-AG according to the present invention is suited for applying to an automated analysis device. That is, according to the method of the present invention, 1,5-AG can be assay using an automated device which could not be made by conventional methods. In addition, a large number of specimen can be handled rapidly and accurately also by assaying many clinical test items.

What is claimed is:

1. A quantitative assay for 1,5-anhydroglucitol in a specimen derived from blood, blood serum, or blood plasma which comprises:

A) treating said specimen with a phosphorylating enzyme in the presence of 5 to 500 mM adenosine-5'-triphosphate to selectively eliminate sugars other than 1,5-anhydroglucitol, B) reacting the solution from step A), with pyranose oxidase derived from *Basidiomycetous fungi* No. 52 in a pH range of 6 to 9 and in the presence the adenosine-5'-triphosphate from step A), and C) measuring the hydrogen peroxide generated in st(ep B);

all of steps A), B), and C) being performed in solution without intermediate separation steps, in one reaction zone.

2. The assay of claim 1, wherein said phosphorylating enzyme is hexokinase.

3. A quantitative assay for 1,5-anhydroglucitol in a specimen derived from blood, blood serum, or blood plasma which comprises:

A) treating said specimen with a phosphorylating enzyme in the presence of 5 to 500 mM adenosine-5'-triphosphate to selectively eliminate sugars other than 1,5-anhydroglucitol, B) reacting the solution from step A) with pyranose oxidase derived from *Basidiomycetous fungi* No. 52 in a pH range of 6 to 9and in the presence of the adenosine-5'-triphosphate from step A), wherein steps A) and B) are conducted at the same pH, and C) measuring the hydrogen peroxide generated in step B);

all of steps A), B), and C) being performed in solution without intermediate separation steps, in one reaction zone.

4. The assay of claim 3, wherein said phosphorylating enzyme is hexokinase.

5. The assay of claim 1, wherein all of steps A), B), and C) are carried out in an automated analysis device.

6. The assay of claim 3, wherein all of steps A), B), and C) are carried out in an automated analysis device.

* * * * *